(12) United States Patent
Bertz et al.

(10) Patent No.: US 6,562,993 B1
(45) Date of Patent: May 13, 2003

(54) PRESERVATIVE COMPOUNDS

(75) Inventors: Steven H. Bertz, Mendham, NJ (US); Samuel T. D'Arcangelis, Randolph, NJ (US); Ilya Makarovskiy, Fair Lawn, NJ (US); John J. Merianos, Middletown, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 10/142,627

(22) Filed: May 10, 2002

(51) Int. Cl.$^7$ .................................................. C07C 255/04
(52) U.S. Cl. ...................................................... 558/384
(58) Field of Search .......................................... 558/384

(56) References Cited

U.S. PATENT DOCUMENTS

| | | | |
|---|---|---|---|
| 3,833,731 A | 9/1974 | Grier et al. | 424/304 |
| 3,877,922 A | 4/1975 | Grier et al. | 424/304 |
| 3,929,858 A | 12/1975 | Swigert | 260/465.7 |
| 4,655,815 A | 4/1987 | Jakubowski | 71/67 |
| 4,964,892 A | 10/1990 | Hsu | 71/67 |
| 5,034,405 A | 7/1991 | Jakubowski | 514/369 |
| 5,942,240 A | 8/1999 | Merianos et al. | 424/405 |

*Primary Examiner*—Taofiq Solola
(74) *Attorney, Agent, or Firm*—Walter Katz; William J. Davis; Marilyn J. Maue

(57) ABSTRACT

The invention relates to preservative compounds having the formula:

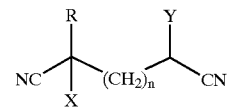

where:

X and Y are H or Br, with at least one of X and Y being Br;

R is H or $CH_3$; and n=1–8; and mixtures thereof.

18 Claims, No Drawings

PRESERVATIVE COMPOUNDS

BACKGROUND OF THE INVENTION

1. Field of the Invention

This invention relates to preservative compounds, and more particularly, to monobromodinitrile and dibromodinitrile compounds having bromine atoms positioned alpha to the nitrile groups, which exhibit excellent preservative activity, and to a method of making such new and useful compounds.

2. Description of the Prior Art

A well-known preservative for personal care products is 1,2-dibromo-2,4-dicyanobutane (also named 2-bromo-2-bromomethylglutaronitrile), which is sold as Merguard® 1200 (Calgon) or Integra® CG-20 (International Specialty Products). This specific dibromodinitrile compound is prepared by adding bromine to the double bond of 2,4-dicyanobutene (α-methyleneglutaronitrile), as shown below:

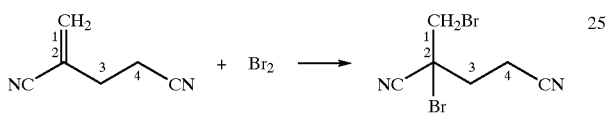

See U.S. Pat. Nos. 3,833,731; 3,877,922; 3,929,858; 4,655,815; 4,964,892 and 5,034,405.

Accordingly, it is an object of this invention to provide new and useful bromodinitrile preservative compounds which exhibit excellent preservative activity in such use compositions as personal care, nutritional, industrial and pharmaceutical compositions, and in which all bromine atoms therein are positioned alpha to a nitrile group.

Another object herein is to provide a method of making such novel preservative compounds.

These and other objects and features of the invention will be made apparent from the following description thereof.

SUMMARY OF THE INVENTION

Described herein are new and active preservative compounds which are particularly useful in personal care, nutritional, industrial and pharmaceutical products, having the general formula:

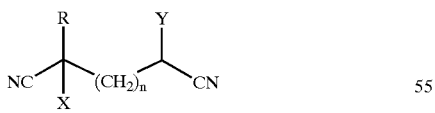

where:
X and Y are H or Br, with at least one of X and Y being Br;
R is H or $CH_3$; and
n=1–8; and
mixtures thereof.

These preservative compounds are particularly characterized by having all bromine atoms positioned alpha to the nitrile groups.

The preferred compounds of the invention are those wherein n=1 or 2.

Specific compounds of the invention have the formulas given below:

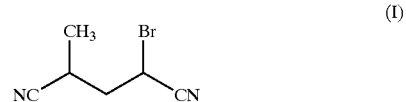

2-bromo-4-methylglutaronitrile

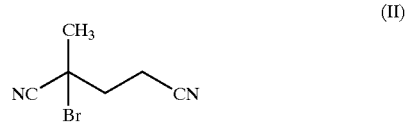

2-bromo-2-methylglutaronitrile

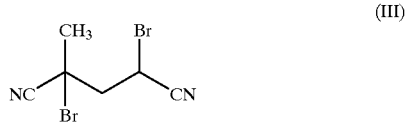

2,4-dibromo-2-methylglutaronitrile

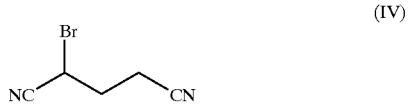

2-bromoglutaronitrile

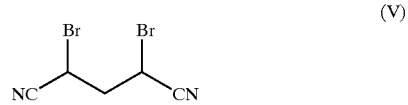

2,4-dibromoglutaronitrile

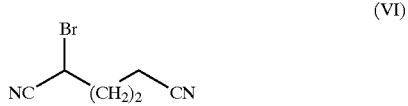

2-bromoadiponitrile

2,5-dibromoadiponitrile

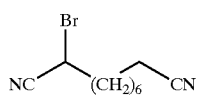

2-bromosebaconitrile

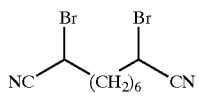

2,9-dibromosebaconitrile

Admixtures of compounds within the general formula, or the specific compounds, are also within the purview of the invention.

The preservative compounds of the invention are made by brominating a compound of the formula:

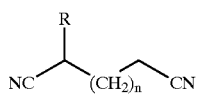

where R and n are as defined above, with one or two equivalents of liquid bromine and a catalytic brominating agent, preferably phosphorus tribromide. For some products, N-bromosuccinimide or 1,5-dibromo-3,3-dimethylhydantoin can be used with a radical initiator (e.g., azobisisobutyronitrile or benzoyl peroxide).

The active preservative compounds of the invention can be included in personal care, nutritional, industrial or pharmaceutical compositions, suitably at advantageous use levels of about 0.01–1 wt %.

The invention will now be described in more detail by reference to the following examples.

EXAMPLE 1

Preparation of Compounds I & II

A 100-mL, 3-neck, round-bottom flask was fitted with a magnetic stirrer, thermometer, condenser with nitrogen inlet, and addition funnel. All glassware was oven-dried. To the reaction flask was added 10.8 g (0.100 mol) of 2-methylglutaronitrile and 20 mL of chloroform, free of protic additives. Stirring was commenced, and 2.65 g (0.0100 mol, 0.945 mL) of phosphorus tribromide was added to the reaction mixture. Heating was carefully adjusted to maintain a minimum reflux temperature of ca. 60–65° C. Bromine (15.9 g, 5.10 mL, 0.110 mol) was added dropwise at such a rate that a minimum of color due to bromine vapor was observed in the condenser (addition time ca. 30 min). Reflux was continued until the bromine vapor disappeared (ca. 60 min). The reaction mixture was allowed to cool to room temperature, and the yellow solids were removed by vacuum filtration through a thin layer of diatomaceous earth. The resulting chloroform solution was added to five times its weight of fresh chloroform in a separatory funnel, and 50 mL of water was added. Sodium sulfite (0.1–1.0 g) was added as needed so that starch/iodide paper tested negative. The aqueous layer was separated, and the chloroform layer was washed with 10% aqueous sodium bicarbonate, dried over 2 g of anhydrous $MgSO_4$ and stripped under reduced pressure. The residue was vacuum distilled twice (100–105° C., 1 torr) to yield 26.7 g (77%) of colorless liquid. Gas chromatography (GC) analysis: 45.7 wt % I & II, 38.4 wt % III, 15.9 wt % 2-methylglutaronitrile.

EXAMPLE 2

Preparation of Compound II

A 1-L, 4-neck, round-bottom flask was fitted with a magnetic stirrer and a condenser with a nitrogen inlet. All glassware was oven-dried. To the reaction flask was added 21.6 g (0.200 mol) of 2-methylglutaronitrile, 200 mL of chloroform (free of protic additives), 142 g (0.400 mol) of N-bromosuccinimide (NBS), and 0.326 g (1.00 mmol) of azobisisobutyronitrile (AIBN). An additional 0.163 g (0.500 mmol) of AIBN was added every 24 hours. The reaction mixture was refluxed continuously for 4 days, when the conversion monitored by GC became constant (80%). The reaction mixture was allowed to cool to room temperature, and 200 mL of water was added to remove the succinimide by-product and excess NBS from the chloroform layer. Sufficient solid sodium sulfite (ca. 10 g) was added so that starch/iodide paper tested negative. The chloroform layer was separated, washed twice with 40 mL of water and dried over 2 g of $MgSO_4$. The chloroform was stripped at 40° C. under reduced pressure, and the residue was vacuum distilled (105–108° C., 1 torr) to yield 17.4 g (46%) of colorless liquid. GC analysis: 93.2 wt % II, 6.8 wt % 2-methylglutaronitrile.

EXAMPLE 3

Preparation of Compound III

A 100-mL, 3-neck, round-bottom flask was fitted with a magnetic stirrer, thermometer, condenser with nitrogen inlet, and addition funnel. All glassware was oven-dried. To the reaction flask was added 10.8 g (0.100 mol) of 2-methylglutaronitrile and 20 mL of chloroform, free of protic additives. Stirring was commenced, and 2.65 g (0.0100 mol, 0.945 mL) of phosphorus tribromide was added. Heating was carefully adjusted to maintain a minimum reflux temperature of ca. 60–65° C. Bromine (31.8 g, 10.2 mL, 0.220 mol) was added dropwise at such a rate that a minimum of color due to bromine vapor was observed in the condenser (addition time ca. 30 min). Reflux was continued until the bromine vapor disappeared (ca. 60 min). The reaction mixture was allowed to cool to room temperature, and the yellow solids were removed by vacuum filtration through a thin layer of diatomaceous earth. The resulting chloroform solution was added to five times its weight of fresh chloroform in a separatory funnel, and 50 mL of water was added. Sodium sulfite (0.1–1.09) was added as needed so that starch/iodide paper tested negative. The aqueous layer was separated, and the chloroform layer was washed with 10% aqueous sodium bicarbonate, dried over 2 g of anhydrous $MgSO_4$ and stripped under reduced pressure. The residue was vacuum distilled twice (100–105° C., 1 torr) to yield 14.8 g (30%) of colorless liquid. GC analysis: 67.6 wt % III, 26.4 wt % I & II, 6.0 wt % 2-methylglutaronitrile.

EXAMPLE 4

Preparation of Compound IV

A 100-mL, 3-neck, round-bottom flask was fitted with a magnetic stirrer, thermometer, condenser with nitrogen inlet, and addition funnel. All glassware was oven-dried. To the reaction flask was added 14.2 g (0.150 mol) of glutaronitrile and 30 mL of chloroform, free of protic additives. Stirring was commenced, and 4.07 g (15.0 mmol, 1.43 mL) of phosphorus tribromide was added. Heating was carefully adjusted to maintain a minimum reflux temperature of ca. 60–65° C. Bromine (26.4 g, 8.48 mL, 0.165 mol) was added dropwise at such a rate that a minimum of color due to bromine vapor was observed in the condenser (addition time ca. 30 min). Reflux was continued until the bromine vapor disappeared (ca. 90 min). The reaction mixture was allowed to cool to room temperature, and the yellow solids were removed by filtration through a thin layer of diatomaceous earth. The resulting chloroform solution was added to five times its weight of fresh chloroform in a separatory funnel, and 50 mL of water was added. Solid sodium sulfite (0.1–1.0 g) was added as needed so that starch/iodide paper tested negative. The aqueous layer was separated, and the chloroform layer was washed with 10% aqueous sodium bicarbonate, dried over 2 g of anhydrous $MgSO_4$ and stripped under reduced pressure. The residue was vacuum distilled twice (105–110° C., 1 torr) to yield 6.6 g (25%) of colorless liquid. GC analysis: 14.4 wt % IV, 0.8 wt % V, 84.8 wt % glutaronitrile.

EXAMPLE 5

Preparation of Compound V

A 100-mL, 3-neck, round-bottom flask was fitted with a magnetic stirrer, thermometer, condenser with nitrogen inlet, and addition funnel. All glassware was oven-dried. To the reaction flask was added 14.2 g (0.150 mol) of glutaronitrile and 30 mL of chloroform, free of protic additives. Stirring was commenced, and 4.07 g (15.0 mmol, 1.43 mL) of phosphorus tribromide was added. Heating was carefully adjusted to maintain a minimum reflux temperature of ca. 60–65° C. Bromine (50.5 g, 16.2 mL, 0.316 mol) was added dropwise at such a rate that a minimum of color due to bromine was observed in the condenser (addition time ca. 30 min). Reflux was continued until the bromine vapor disappeared (ca. 90 min). The reaction mixture was allowed to cool to room temperature, and the yellow solids were removed by filtration through a thin layer of diatomaceous earth. The resulting chloroform solution was added to five times its weight of fresh chloroform in a separatory funnel, and 50 mL of water was added. Solid sodium sulfite (0.1–1.0 g) was added as needed so that starch/iodide paper tested negative. The aqueous layer was separated, and the chloroform layer was washed with 10% aqueous sodium bicarbonate, dried over 2 g of anhydrous $MgSO_4$ and stripped under reduced pressure. The residue was vacuum distilled twice (100–110° C., 1 torr) to yield 9.9 g (26%) of colorless liquid. GC analysis: 39.2 wt % V, 18.4 wt % IV, 42.4 wt % glutaronitrile.

EXAMPLE 6

Preparation of Compounds VI & VII

A 100-mL, 3-neck, round-bottom flask was fitted with a magnetic stirrer, thermometer, condenser with nitrogen inlet, and addition funnel. All glassware was oven-dried. To the reaction flask was added 16.2 g (0.150 mol) of adiponitrile and 30 mL of chloroform, free of protic additives. Stirring was commenced, and 4.06 g (15.0 mmol, 1.43 mL) of phosphorus tribromide was added. Heating was carefully adjusted to maintain a minimum reflux temperature of ca. 60–65° C. Bromine (50.4 g, 16.2 mL, 0.316 mol) was added dropwise at such a rate that a minimum of color due to bromine was observed in the condenser (addition time ca. 30 min). Reflux was continued until the bromine vapor disappeared (ca. 90 min). The reaction mixture was allowed to cool, and the yellow solids were removed by filtration through a thin layer of diatomaceous earth. The resulting chloroform solution was added to ten times its weight of fresh chloroform in a separatory funnel, and 50 mL of water was added. Solid sodium sulfite (0.1–1.0 g) was added as needed so that starch/iodide paper tested negative. The aqueous layer was separated, and the chloroform layer was washed with 10% aqueous sodium bicarbonate, dried over 2 g of anhydrous $MgSO_4$ and stripped under reduced pressure. The residue was vacuum distilled twice (105–110° C., 1 torr) to yield 10.1 g (25%) of colorless liquid. GC analysis: 44.8 wt % VI, 8.4 wt % VII, 46.9 wt % adiponitrile.

EXAMPLE 7

Preparation of Compounds I, II & III

A 1-liter, 4-neck, round-bottom flask was fitted with a mechanical stirrer, thermometer, condenser with nitrogen inlet, and addition funnel. All glassware was oven-dried. The reaction flask was charged with 108 g (1.00 mol) of 2-methylglutaronitrile, and 2.71 g (10.0 mmol, 0.950 mL) of phosphorus tribromide was added with stirring. The reaction mixture was slowly heated to 80° C., and 79.9 g (0.500 mol, 25.6 mL) of bromine was added dropwise to the reaction mixture at such a rate that the temperature was maintained at 80–85° C. (ca. 90 min). The reaction mixture was allowed to cool below 60° C., and 250 mL of chloroform was added. Upon cooling to room temperature, 31.5 g of precipitate formed and was collected by vacuum filtration. The chloroform solution was washed three times with 100 mL of water and transferred to a 1-L Erlenmeyer flask containing a large magnetic stirbar. It was cooled to 0° C. with an ice bath, and 37.3 g of concentrated sulfuric acid was added dropwise with efficient stirring. The dark, viscous mass that formed was allowed to settle, and the chloroform phase was decanted to a separatory funnel. It was washed twice with 100 mL of ice-cold water, dried over 3.5 g of $MgSO_4$, filtered and stripped under reduced pressure to yield 39.9 g (42%) of pale yellow liquid. GC analysis: 52.1 wt % I & II, 12.8 wt % III, 35.0 wt % 2-methylglutaronitrile.

EXAMPLE 8

Preparation of Compounds IV & V

A 500-mL, 4-neck, round-bottom flask was fitted with a mechanical stirrer, thermometer, condenser with nitrogen inlet, and addition funnel. All glassware was oven-dried. The flask was charged with 94.1 g (1.00 mol) of glutaronitrile, and 2.71 g (10.0 mmol, 0.950 mL) of phosphorus tribromide was added with stirring. The reaction mixture was slowly heated to 90° C., and 159 g (1.00 mol, 51.2 mL) of bromine was added dropwise to the reaction mixture at such a rate that the temperature was maintained at 90–95° C. (ca. 90 min). The reaction mixture was allowed to cool below 60° C., and 250 mL of chloroform was added. Upon cooling to room temperature, 158 g of precipitate formed and was collected by vacuum filtration. The chloroform solution was washed three times with 100 mL of water and transferred to a 500-mL Erlenmeyer flask containing a large magnetic stirbar. It was cooled to 0° C. with an ice bath, and 30.0 g of concentrated sulfuric acid was added dropwise with efficient stirring. The dark, viscous mass that formed was allowed to settle, and the chloroform phase was decanted to a separatory funnel. It was washed twice with 100 mL of ice-cold water, dried over 3.0 g of $MgSO_4$, filtered and stripped under reduced pressure to yield 41.5 g (24%) of pale yellow liquid. GC analysis: 55.9 wt % IV, 31.6 wt % V, and 12.5 wt % glutaronitrile.

EXAMPLE 9

Preparation of Compounds VIII & IX

A 250-mL, 4-neck, round-bottom flask was fitted with a mechanical stirrer, thermometer, condenser with nitrogen inlet, and addition funnel. The reaction flask was charged with 49.3 g (0.300 mol) of sebaconitrile, and 0.812 g (3.00 mmol, 0.285 mL) of phosphorus tribromide was added with stirring. The reaction mixture was slowly heated to 90° C., and 47.9 g (0.300 mol, 15.4 mL) of bromine was added dropwise at such a rate that the temperature was maintained at 90–95° C. (ca. 90 min). The reaction mixture was allowed to cool below 60° C., and 100 mL of chloroform was added. Upon cooling to room temperature, the chloroform solution was washed twice with 50 mL of water and transferred to a 250-mL Erlenmeyer flask containing a large magnetic stirbar. It was cooled to 0° C. with an ice bath, and 12.7 g of concentrated sulfuric acid was added dropwise with efficient stirring until a separate phase formed. The sulfuric acid phase was separated from the chloroform at ca. 0° C. in a separatory funnel. The chloroform solution was washed twice with 50 mL of ice-cold water, dried over 2.0 g of MgSO$_4$, filtered and stripped under reduced pressure to yield 60.8 g (50%) of pale yellow liquid. GC analysis: 52.4 wt % VIII, 26.4 wt % IX, and 21.2 wt % sebaconitrile.

Evaluation of Bromo Compounds

The Minimum Inhibitory Concentration (MIC) Test is an in vitro serial dilution procedure to assess antimicrobial activity. The MIC of a substance is the minimum concentration that will inhibit the growth of test organisms. Two species each of bacteria and fungi were included in the evaluation.

| Bacteria | Inoculum (conc. in dilution tube) |
| --- | --- |
| Staphylococcus aureus ATCC 6538 | 3.0 × 10$^5$ cfu/mL |
| Burkholderia cepacia ATCC 25416 | 2.6 × 10$^5$ cfu/mL |
| Fungi | Inoculum (conc. in dilution tube) |
| Candida albicans ATCC 10231 | 1.6 × 10$^5$ cfu/mL |
| Aspergillus niger ATCC 16404 | 5.0 × 10$^4$ cfu/mL |

Cultiloop™ transfer cultures were used, and the bacteria were cultured on Brain Heart Infusion agar for 24 hours at 37° C. A saline suspension of each bacterial species was prepared and standardized on the spectrophotometer to the organism inoculum concentration. The yeast culture (Candida) was grown on a slant of Saboraud Dextrose agar for 48 hours at 27° C., and the slant was then washed with saline to prepare the inoculum. The mold culture (Aspergillus) was incubated for 7–10 days at 27° C. until sporulation occurred. The mold inoculum was prepared by washing the mature slant and harvesting the spores after filtration through sterile gauze.

MIC testing of selected bromo-compounds of the invention, and of Merguard® standard, in propylene glycol solvent using routine methods showed that these compounds were antimicrobial to the organisms screened at low concentrations. They were substantially comparable in activity to the standard. The results are summarized in the Table below, where the concentrations refer to the weight percents of active ingredients.

TABLE

MIC test results for bromonitrile compounds.

| Test Material | Organism | Static | Cidal |
| --- | --- | --- | --- |
| Compounds I, II & III | S. aureus | <0.05% | <0.05% |
| | B. cepacia | <0.05% | <0.05% |
| | C. albicans | <0.05% | <0.05% |
| | A. niger | <0.05% | <0.05% |
| Compound II | S. aureus | <0.05% | 0.10% |
| | B. cepacia | <0.05% | <0.05% |
| | C. albicans | <0.05% | <0.05% |
| | A. niger | <0.05% | 0.10% |
| Compounds IV & V | S. aureus | <0.05% | <0.05% |
| | B. cepacia | <0.05% | <0.05% |
| | C. albicans | <0.05% | <0.05% |
| | A. niger | <0.05% | <0.05% |
| Compounds VI & VII | S. aureus | <0.05% | 0.10% |
| | B. cepacia | <0.05% | <0.05% |
| | C. albicans | <0.05% | <0.05% |
| | A. niger | <0.05% | 0.10% |
| Merguard ® | S. aureus | <0.05% | <0.05% |
| | B. cepacia | <0.05% | <0.05% |
| | C. albicans | <0.05% | <0.05% |
| | A. niger | <0.05% | <0.05% |

What is claimed is:

1. A preservative compound having the formula:

$$NC-\underset{X}{\overset{R}{C}}-(CH_2)_n-\underset{}{\overset{Y}{C}}-CN$$

where:

X and Y are H or Br, with one of X and Y being Br;

R is H or CH$_3$; and n=1–8; and mixtures thereof.

2. A compound according to claim 1 wherein X=Br.

3. A compound according to claim 1 wherein Y=Br.

4. A compound according to claim 1 wherein R=H.

5. A compound according to claim 1 wherein R=CH$_3$.

6. A compound according to claim 1 wherein n=1 or 2.

7. A compound according to claim 1 having the formula:

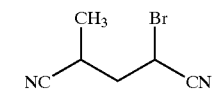

2-bromo4-methylglutaronitrile.

8. A compound according to claim 1 having the formula:

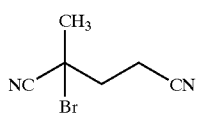

2-bromo-2-methylglutaronitrile.

9. A compound according to claim 1 having the formula:

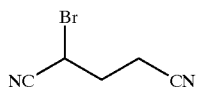

2-bromoglutaronitrile.

10. A compound according to claim 1 having the formula:

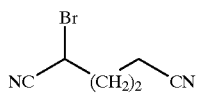

2-bromoadiponitrile.

11. A method of making a compound of claim 1 which comprises brominating a compound of the formula:

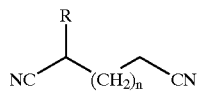

where R and n are as defined in claim 1.

12. A method according to claim 11 wherein R=H.

13. A method according to claim 11 wherein $R=CH_3$.

14. A method according to claim 11 wherein n=1 or 2.

15. A method according to claim 11 wherein said brominating agent is selected from one of the following: a mixture of liquid bromine and catalytic phosphorus tribromide; N-bromosuccinimide or 1,5-dibromo-3,3-dimethylhydantoin.

16. A composition further comprising a preservative compound of claim 1.

17. A personal care, nutritional, industrial or pharmaceutical composition further comprising a preservative compound of claim 1.

18. A composition according to claim 17 in which said preservative compound is present therein in an amount of 0.01–1 wt %.

* * * * *